US006441377B1

United States Patent
Hug et al.

(10) Patent No.: US 6,441,377 B1
(45) Date of Patent: Aug. 27, 2002

(54) SYSTEM FOR EXCHANGING AND STORING COLLIMATORS FOR MEDICAL IMAGING DEVICES

(75) Inventors: Paul Hug, Saratoga; Rizwan Hassan, Fremont; Moataz Karmalawy, San Ramon, all of CA (US)

(73) Assignee: Koninklijke Philips Electronics N.V. (NL)

( * ) Notice: Subject to any disclaimer, the term of this patent is extended or adjusted under 35 U.S.C. 154(b) by 0 days.

(21) Appl. No.: 09/448,567

(22) Filed: Nov. 23, 1999

(51) Int. Cl.[7] .......................... G21K 1/02; G01T 1/166
(52) U.S. Cl. .................... 250/363.1; 250/363.05
(58) Field of Search .................... 250/363.1, 363.05, 250/505.1

(56) References Cited

U.S. PATENT DOCUMENTS

| 3,982,133 A | * | 9/1976 | Jupa et al. ............... 250/505.1 |
| 4,109,155 A | * | 8/1978 | Tschunt et al. .......... 250/505.1 |
| 4,663,531 A | * | 5/1987 | Ruike ...................... 250/505.1 |
| 5,519,223 A | * | 5/1996 | Hug et al. ............... 250/363.1 |

* cited by examiner

Primary Examiner—Ricky Mack
Assistant Examiner—Alicia M Harrington
(74) Attorney, Agent, or Firm—Eugene E. Clair

(57) ABSTRACT

A system for exchanging and storing collimators for medical imaging devices includes a first frame having a first receptacle and a second frame having a first docking member. A collimator can be attached to and removed from the first receptacle. The first docking member can be positioned adjacent to the first receptacle such that the first docking member can contact the collimator to remove the collimator from the first receptacle. The collimator is coupled to the first docking member while the collimator is removed from the first receptacle.

28 Claims, 13 Drawing Sheets

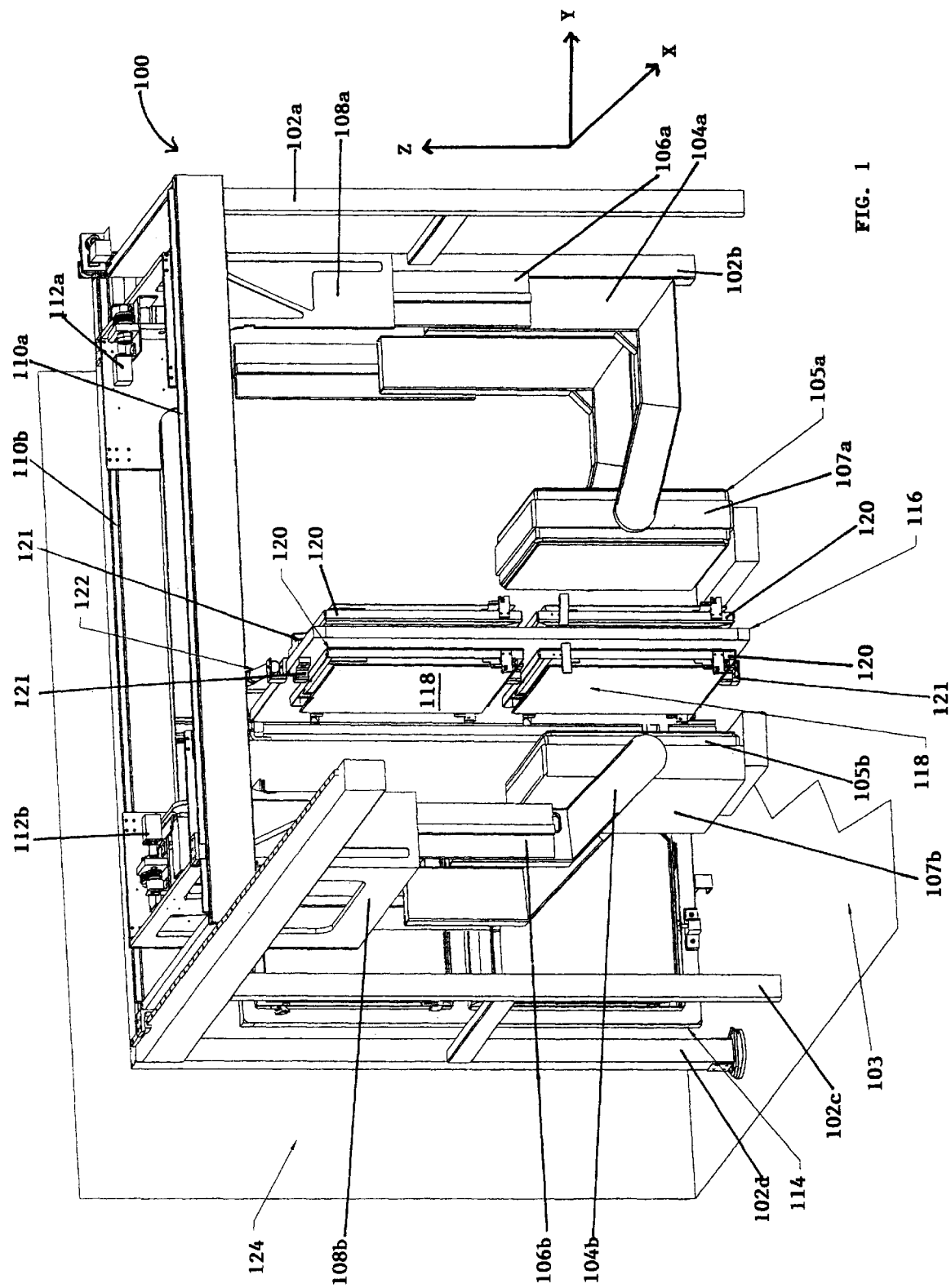

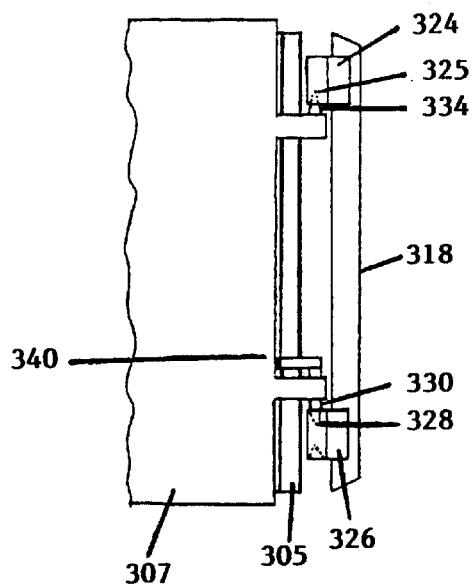
FIG. 4B
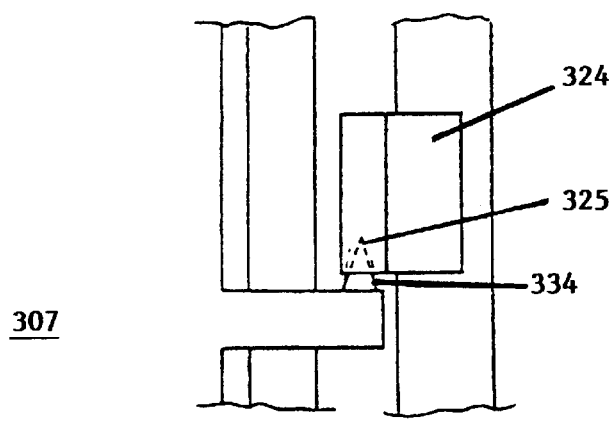
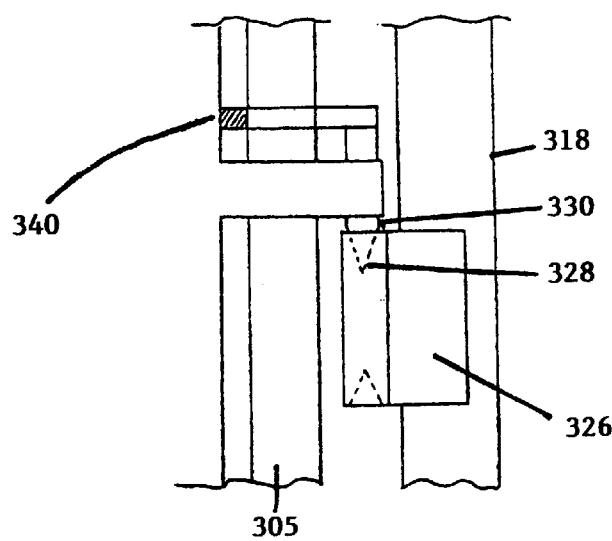
FIG. 4C

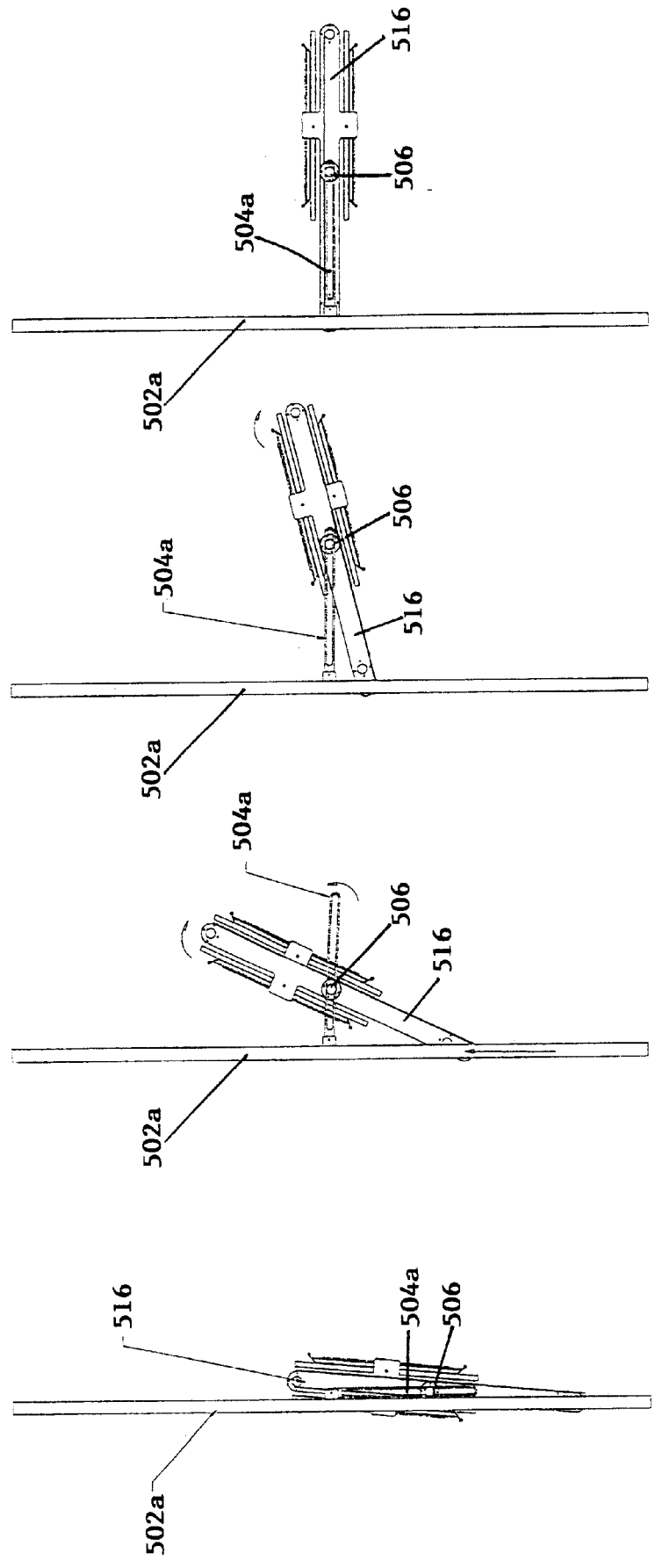

SYSTEM FOR EXCHANGING AND STORING COLLIMATORS FOR MEDICAL IMAGING DEVICES

BACKGROUND OF THE INVENTION

1. Field of the Invention

The present invention relates generally to medical imaging systems, and more specifically to collimator exchange and storage systems for nuclear medicine imaging devices.

2. Background Information

Conventional nuclear medicine imaging systems include one or more gamma ray detectors supported by a gantry. The gantry may provide mechanical movement of the detectors such that the detectors can be positioned in different orientations around a patient's body. This allows image data to be acquired from varying angles around the patient.

Some gamma ray imaging systems use the principle of absorptive collimation to form images. Collimators used in absorptive collimation project an image of the source onto a detector by allowing only the gamma rays traveling in certain directions to reach the detector. Typically, a collimator is mounted to the imaging surface of a detector to selectively filter radiation reaching the imaging surface. Different types of collimators can be used to generate images of varying quality and size. Furthermore, certain types of collimators are better suited for particular imaging studies. When different collimators are used during an imaging session or between imaging sessions, the collimators need to be substituted for one another because each detector is paired with only one collimator at a time.

Exchanging collimators using conventional techniques and systems can be inconvenient and potentially dangerous due to the size and weight of the collimators. Many existing systems do not allow a patient to remain on the imaging table while an exchange is performed. Thus, in many existing systems, the patient must be moved off the imaging table when collimators need to be exchanged. However, repeatedly moving the patient to and from the imaging table whenever a collimator exchange is to be made can be time-consuming and harmful to the patient if the patient is in poor physical condition. Furthermore, many existing collimator exchange systems use carts which are heavily weighted when loaded, making it difficult for the operator to maneuver the carts into position. Such carts also occupy valuable floor space when in use or in storage.

A desirable collimator exchange system would allow more imaging sessions to be performed while allowing the patient to remain on the imaging table and not wait any longer than necessary. A desirable collimator exchange system would also conserve floor space.

SUMMARY OF THE INVENTION

The present invention provides an apparatus for exchanging collimators. In one embodiment of the present invention, the apparatus includes a first frame having a first receptacle and a second frame having a first docking member. A collimator can be attached to and removed from the first receptacle. The first docking member can be positioned adjacent to the first receptacle such that the first docking member can contact the collimator to remove the collimator from the first receptacle. The collimator is coupled to the first docking member while the collimator is removed from the first receptacle.

In another embodiment of the present invention, the apparatus for exchanging collimators includes first and second transfer members which are movably coupled to a housing, and a rotatable delivery arm having a first collimator coupled to a first side and a second collimator coupled to a second side. The delivery arm rotates from a first position to a second position when one or both of the collimators are to be transferred to the transfer members. When the delivery arm is in the second position, the transfer members are located adjacent to the collimators to be transferred. The transfer members can concurrently uncouple the first and second collimators from the delivery arm when the delivery arm is in the second position.

In yet another embodiment of the present invention, the delivery arm stores the collimators in a vertical plane, such as adjacent to a wall, to reduce the amount of occupied floor space. The delivery arm can be manually or automatically operated.

Additional features and benefits of the present invention will become apparent upon review of the following description.

BRIEF DESCRIPTION OF THE DRAWINGS

Various embodiments of the present invention will be described in detail with reference to the following drawings in which like reference numerals refer to like elements. The present invention is illustrated by way of example and not limitation in the accompanying figures.

FIG. 1 shows a collimator exchanger in conjunction with a gantry system in accordance with the teachings of the present invention.

FIGS. 4B–4C show side views of a detector and collimator after an exchange has been made in accordance with the teachings of the present invention.

FIGS. 7A–7D show the collimator exchanger shown in FIG. 6 in different positions as the exchanger moves to an exchange position in accordance with the teachings of the present invention.

DETAILED DESCRIPTION

Figure 2A:
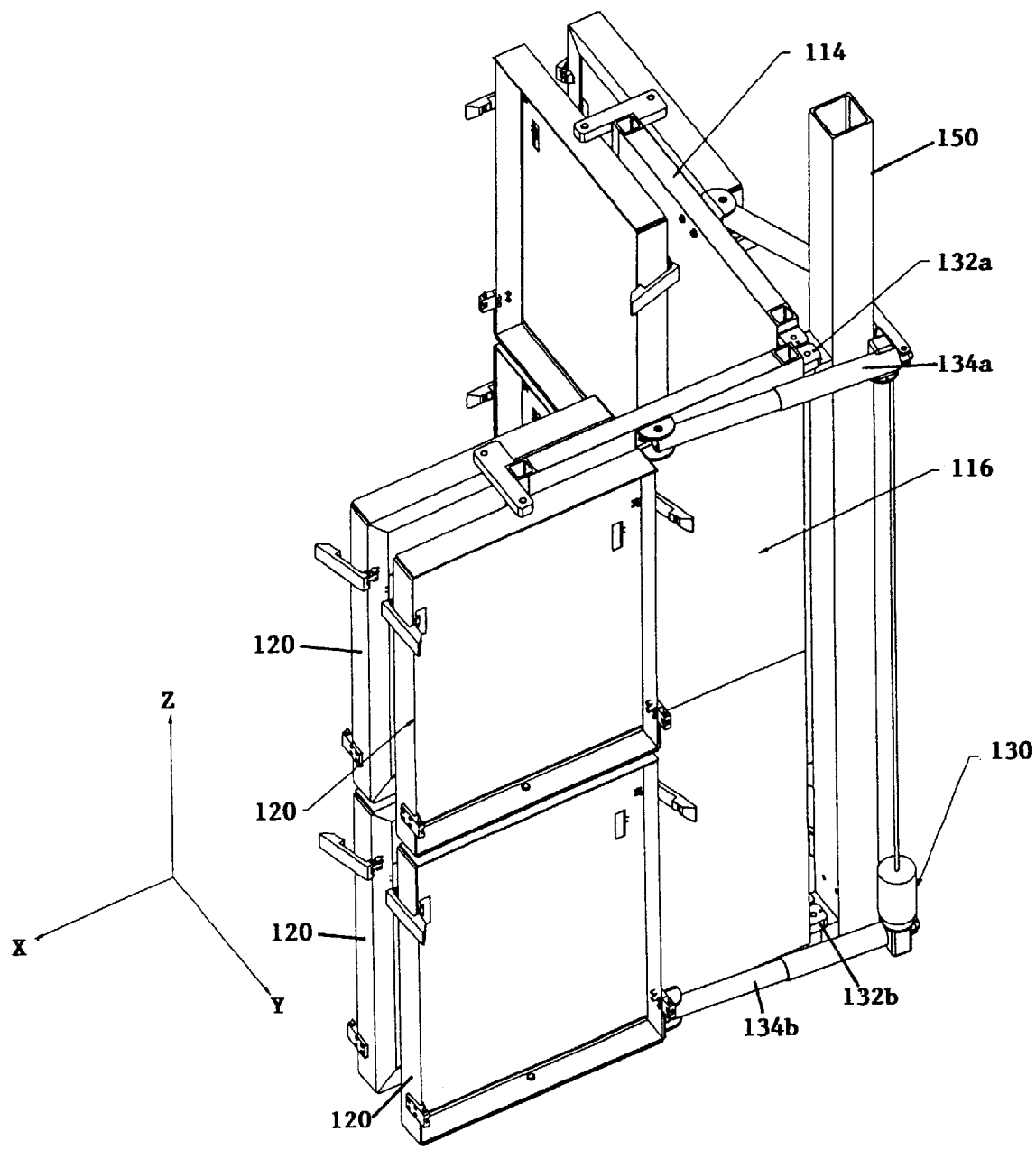
FIG. 2A shows a collimator exchanger in accordance with the teachings of the present invention.

In one embodiment of the present invention, a system for exchanging collimator includes a delivery gate having a first receptacle and a positioning arm having a first docking member. A first collimator, such as those used in absorptive collimation, can be attached to and removed from the first receptacle. When the delivery gate is moved to an exchange area, the first docking member can be positioned adjacent to the first receptacle such that the first docking member can engage the first collimator to remove the first collimator from the first receptacle. The first collimator is secured to the first docking member while the first collimator is removed from the first receptacle. Thus, the first collimator provided by the delivery gate is transferred from the first receptacle to the first docking member.

A second collimator can be attached to and removed from a second receptacle on the delivery gate. When the second collimator is to be engaged with the first docking member, the delivery gate moves back to the exchange area to allow the positioning arm to move the first docking member adjacent to the first receptacle such that the first collimator can be transferred from the first docking member back to the first receptacle. Once the first collimator has been transferred back to the first receptacle, the first docking member is free to engage the second collimator in a manner similar to that previously described with respect to the first collimator.

The delivery gate of the present invention is capable of maintaining a thin profile to conserve space while an imaging session is being conducted. This permits less obtrusive storage of collimators. The thin profile capability also allows the delivery gate to be located near the positioning arm to reduce the time needed for an exchange. Furthermore, because different collimators can be carried by the delivery gate, multiple exchanges can be made using the same gate to reduce the time needed for all exchanges. The present invention also allows a patient to remain on the examination table during an exchange because the exchange area is located away from the patient. This particularly benefits fragile patients whose conditions would be exacerbated if they had to repeatedly move on and off the imaging table.

FIG. 1 shows one embodiment of a collimator exchanger in conjunction with a gantry system. A gantry 100 is supported by legs 102a–102d which rest on a level surface 103, such as a floor. Gantry 100 includes a pair of positioning arms 104a and 104b slidably coupled to connecting arms 106a and 106b, respectively, which are coupled to housings 108a and 108b, respectively. Housings 108a and 108b are supported by guide rails 110a and 110b. Motors 112a and 112b independently drive housings 108a and 108b, respectively, along guide rails 110a and 110b. Positioning arms 104a and 104b are coupled to support frames 107a and 107b, respectively, which contain radiation detectors 105a and 105b. Support frames 107a and 107b can be rotated within positioning arms 104a and 104b, respectively, around the X-axis.

The previous paragraph describes generally a gantry system that can be used with the collimator exchanger of the present invention. More detailed descriptions of suitable gantries similar to the one shown in FIG. 1 are disclosed in U.S. patent application Ser. No. 09/071,367, now U.S. Pat. No. 6,150,662, filed on Apr. 30, 1998, titled "Gantry for Medical Imaging System" by Hug et al., which is incorporated by reference herein.

The collimator exchanger shown in FIG. 1 includes two gates 114 and 116. Gate 114 is shown in a home or closed position, and gate 116 is shown in an exchange or open position. An actuator 122 coupled to gate 116 controls the movement of gate 116 between its home position and its exchange position. Collimator carriers 120 are coupled to support blocks 121 which are fixed to gate 116 and gate 114. Each carrier 120 houses a collimator 118 that can be paired with detectors 105a and 105b to conduct an imaging session. When a gate is in its exchange position, it is oriented such that the face of a detector can be located substantially parallel to the face of a collimator. In FIG. 1, such orientation is parallel to the X-Z plane formed by the X and Z axes. It is appreciated that each carrier can house a different collimator. Alternatively, carriers that are adjacent to each other on opposite sides of a gate can house identical collimators. As described in more detail below, collimators 118 are exchanged from carriers 120 to frames 107a and 107b to pair with detectors 105a and 105b when different images of the patient are required. Before a new collimator is paired with a detector, a presently paired collimator is unpaired from the detector and moved back to its carrier. In one embodiment of the present invention, the exchanger is affixed to a wall 124 adjacent to gantry 100.

The locations of collimators 118 when gates 116 and 114 are in their exchange positions are known by control software which dictates the positioning of detectors 105a and 105b. Thus, when an exchange is to be made, the control software moves detectors 105a and 105b to positions determined by the known locations of collimators 118. This provides automation of the actual collimator exchange upon an operator's selection of a desired collimator to be exchanged. Alternatively, the positioning of detectors 105a and 105b can be operator controlled or a combination of both operator and software controlled.

FIG. 2A shows in isolation a collimator exchanger similar to that shown in FIG. 1. Gate 116 is hinged to post 150 via hinge joints 132a and 132b. Gate 114 is similarly hinged to post 150. Actuator arms 134a and 134b coupled to gate 116 are driven by a linear actuator drive motor 130, which typically works in conjunction with a ramp up and down circuit. Gate 114 is coupled to another pair of actuator arms, similar to actuator arms 134a and 134b, which are also driven by a linear actuator drive motor (not shown), similar to motor 130. In one embodiment of the present invention, the movement of gates 114 and 116 is controlled by switches (not shown) on each gate 114 and 116 that turn on or off the respective motors. Thus, gates 114 and 116 can be moved independently. Control software may prevent gates 114 and 116 from moving to their exchange positions at the same time. It should be noted that carriers 120 are shown without collimators. Furthermore, the number of carriers 120 on gates 114 and 116 may vary depending on the size of gates 114 and 116 and/or the number of desired exchanges, among other factors.

Figure 2B:
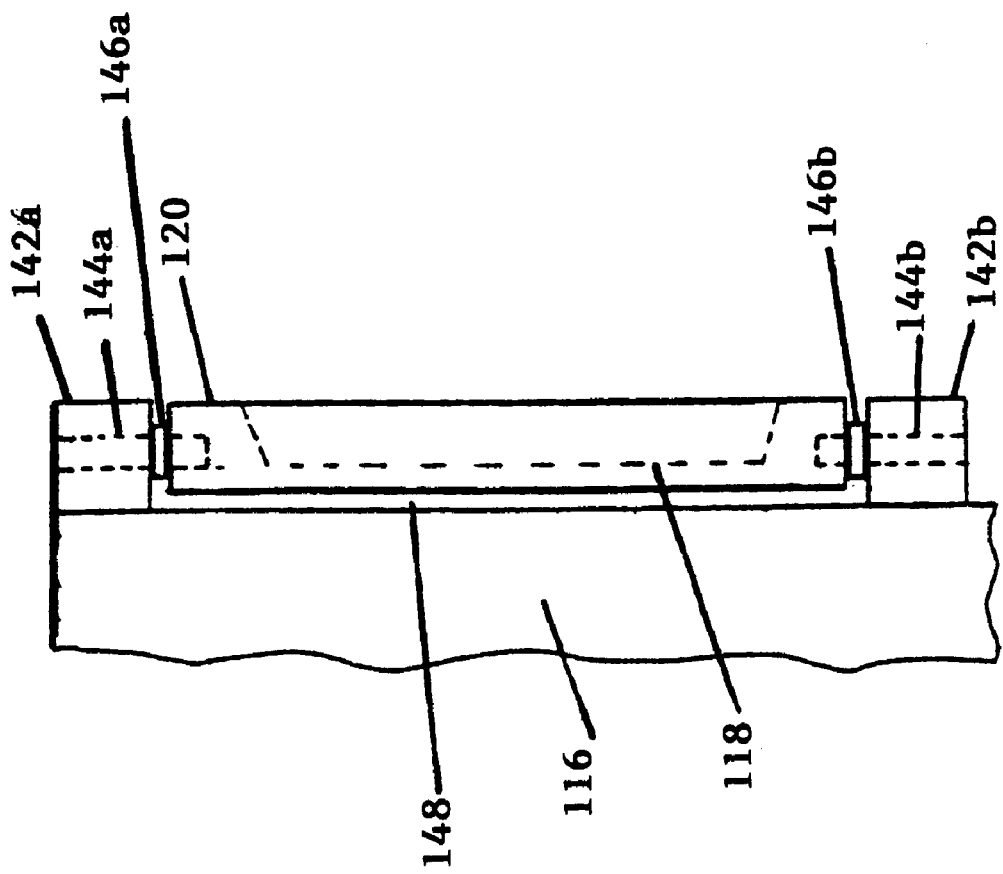
FIG. 2B shows a side view of a collimator carrier used in the exchanger shown in FIG. 2A.

FIG. 2B shows a side view of one carrier 120 and gate 116. Carrier 120 is coupled to support blocks 142a and 142b by pivot pins 144a and 144b, respectively. Support blocks 142a and 142b are attached to gate 116. Spacers 146a and 146b provide separation between carrier 120 and support blocks 142a and 142b. The back surface of carrier 120 is also separated from gate 116 by gap 148. Pivot pins 144a and 144b and gap 148 allow carrier 120 to rotate slightly to assist in aligning with detectors 105a and 105b when collimator 118 is to be exchanged. The rotational aligning of carrier 120 is helpful but not necessary to the present invention. Thus, it is appreciated that carrier 120 can be directly coupled to gate 116 or integrally formed with gate 116.

Figure 3:
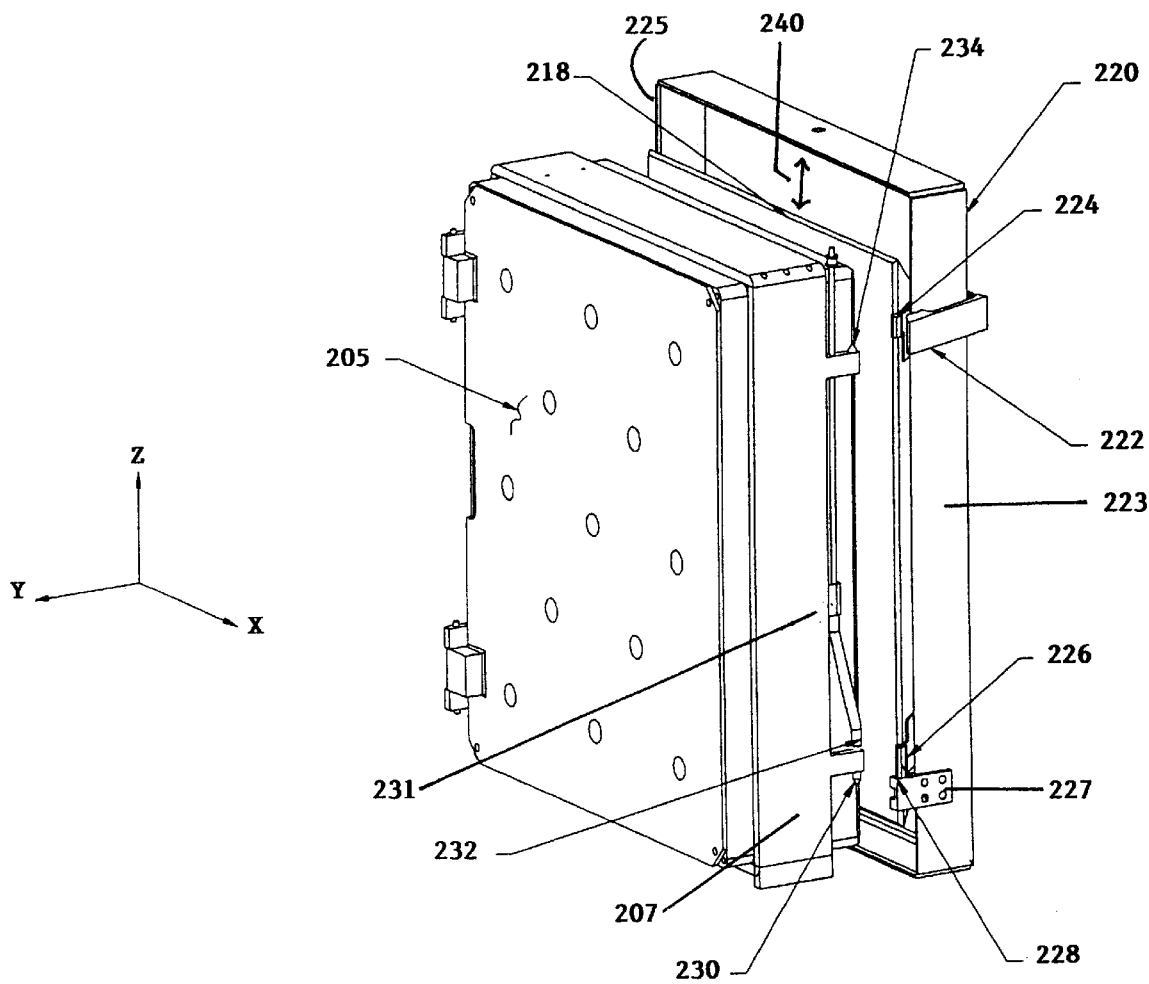
FIG. 3 shows a radiation detector and a collimator in exchange positions in accordance with the teachings of the present invention.

FIG. 3 shows a radiation detector 205 within a support frame 207, and a collimator 218 in exchange positions. A carrier 220 houses collimator 218. Deflectable latches 222 (only one shown) coupled to edges 223 and 225 of carrier 220 help prevent collimator 218 from falling out of carrier 220. In one embodiment of the present invention, the deflectable latches are spring loaded and have angled edges to more easily permit forcible deflection. Collimator 218 is also held in place within carrier 220 by lower pins 228 (only one shown) on carrier 220 mating with lower receptors 226 (only one shown) extending from opposite edges of collimator 218. When collimator 218 is held within carrier 220, a gap 240 exists between the top edge of collimator 218 and the inner top edge of carrier 220 to provide clearance for the exchange of collimator 218 between carrier 220 and frame 207. Pins 228 extend in the Z-direction from tabs 227 (only one shown) coupled to edges 223 and 225 of carrier 220. Tabs 227 can be welded to, adhesively affixed to, or screwed onto edges 223 and 225. Receptors 226 can be similarly coupled to collimator 218.

Upper receptors 224 (only one shown) coupled to opposite edges of collimator 218 are adapted to receive pins 234 (only one shown) extending from frame 207. Pins 234 mate with receptors 224 when collimator 218 is to be exchanged from carrier 220 to frame 207. Pins 230 (only one shown) also mate with receptors 226 to help secure collimator 218 to detector 205. In one embodiment of the present invention, pins 230 are driven downward by linear motors 231 (only one shown) to effectively engage pins 230 with receptors 226. It should be noted that the pins and receptors mate with each other in a male-female connection, as shown in later figures.

Furthermore, the pins have embedded Hall effect sensors and the corresponding targets are located on the receptors that mate with the pins. Hall effect sensors at point 232 on pins 230 signal the position of pins 230 when they are not engaged with receptors 226. Hall effect sensors embedded in the lower portion of pins 230 signal the engaged position of pins 230. When the sensors in pins 234 and in the lower portion of pins 230 are enabled (engaged positions are registered), detector 205 is moved away from carrier 220 in the Y-direction such that collimator 218 deflects latches 222 and is removed from carrier 220. In another embodiment of the present invention, the sensors are embedded in the receptors and the corresponding targets are located on the pins.

Figure 4A:
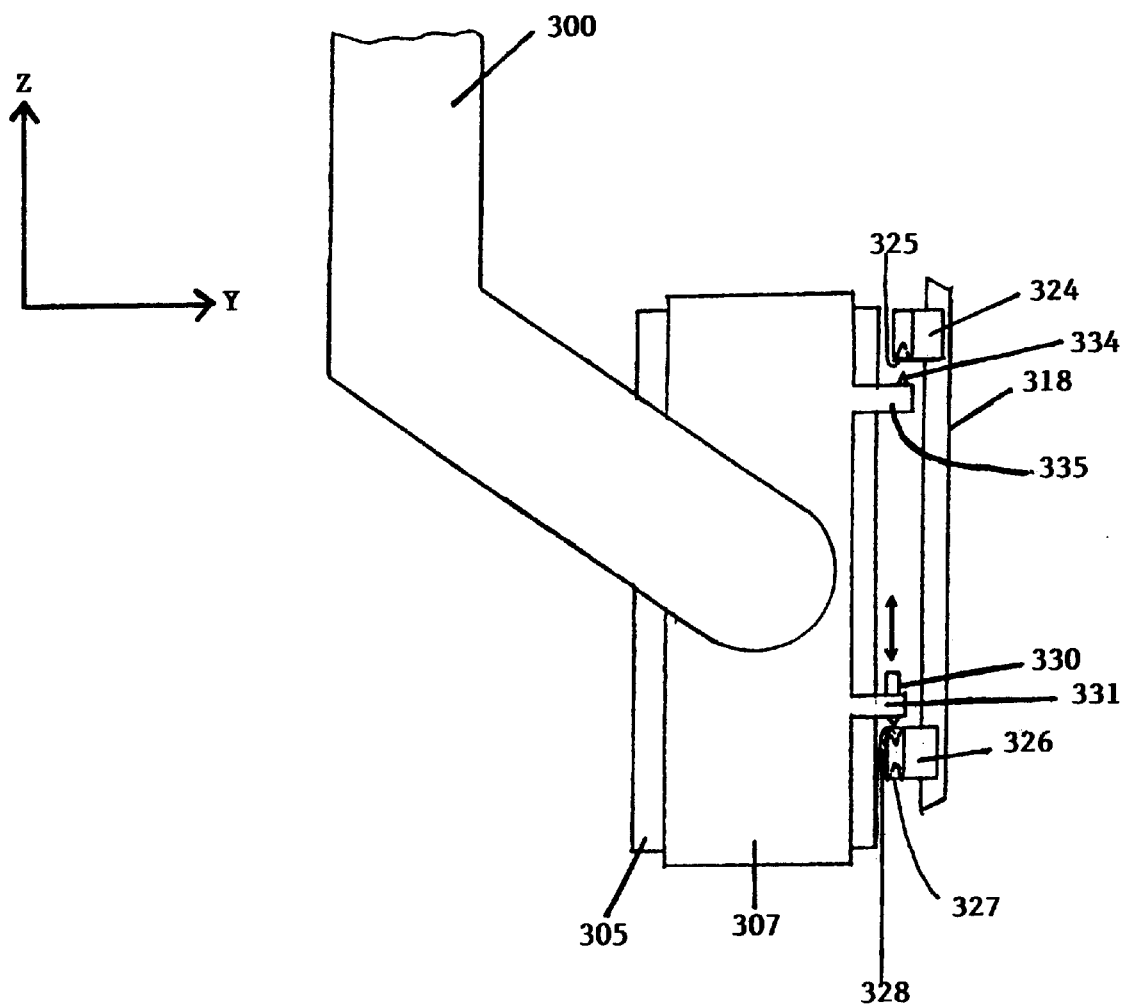
FIG. 4A shows a side view of a detector and a collimator in exchange positions in accordance with the teachings of the present invention.

FIGS. 4A–4C show side views of a radiation detector 305 within a support frame 307, and a collimator 318 in exchange positions. It should be noted that collimator 318 is shown without a carrier. A positioning arm 300 extending from a gantry (not shown) is coupled to frame 307. Arm 300 is capable of movement along the Y and Z axes, as previously described with reference to FIG. 1, such that detector 305 and frame 307 can be moved to and from their exchange positions next to collimator 318. A pin 334 extends from a top surface of a tab 335 of frame 307. A tab 324 extending from an edge of collimator 318 has an indentation 325 that is deep enough to provide a secure fit between pin 334 and indentation 325 when pin 334 is engaged with indentation 325. A movable pin 330 extends through a through hole in a tab 331 of frame 307. In one embodiment of the present invention, the movement of pin 330 is controlled by a linear motor 340. A tab 326 extending from an edge of collimator 318 has an indentation 328 that is deep enough to provide a secure fit between pin 330 and indentation 328 when pin 330 is engaged with indentation 328. Tab 326 also has an indentation 327 for engaging a pin on a carrier when collimator 318 is held within the carrier.

When collimator 318 is to be transferred to frame 307, arm 300 positions frame 307 adjacent to collimator 318 such that pin 334 is located just below tab 324. It should be noted that during this time pin 300 is raised to avoid hitting tab 326 and to allow frame 307 to be moved into its exchange position. Once pin 334 is just below tab 324 and aligned with indentation 325, arm 300 moves up in the Z-direction to engage pin 334 with indentation 325. Once pin 334 is engaged with indentation 325, pin 330 is moved down by motor 340 to engage indentation 328. When all of the pins on frame 307 have engaged their corresponding indentations on the collimator tabs, arm 300 moves along the Z-axis and Y-axis to disengage collimator 318 from its carrier. It should be noted that the mating of the pins and indentations is typically facilitated with sensors as previously described with reference to FIG. 3.

Figure 5A:
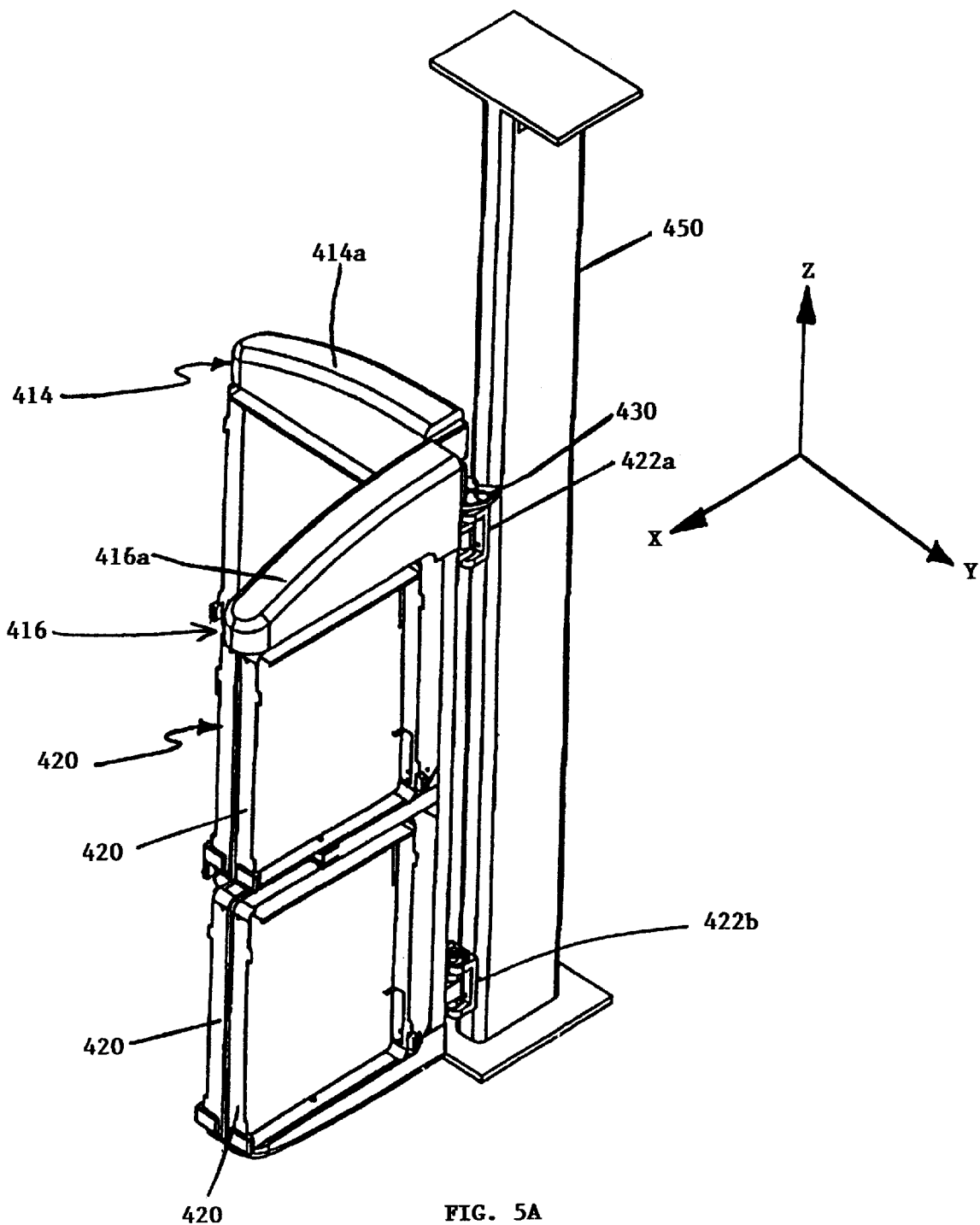
FIGS. 5A–5C show another collimator exchanger in accordance with the teachings of the present invention.
Figure 5B:
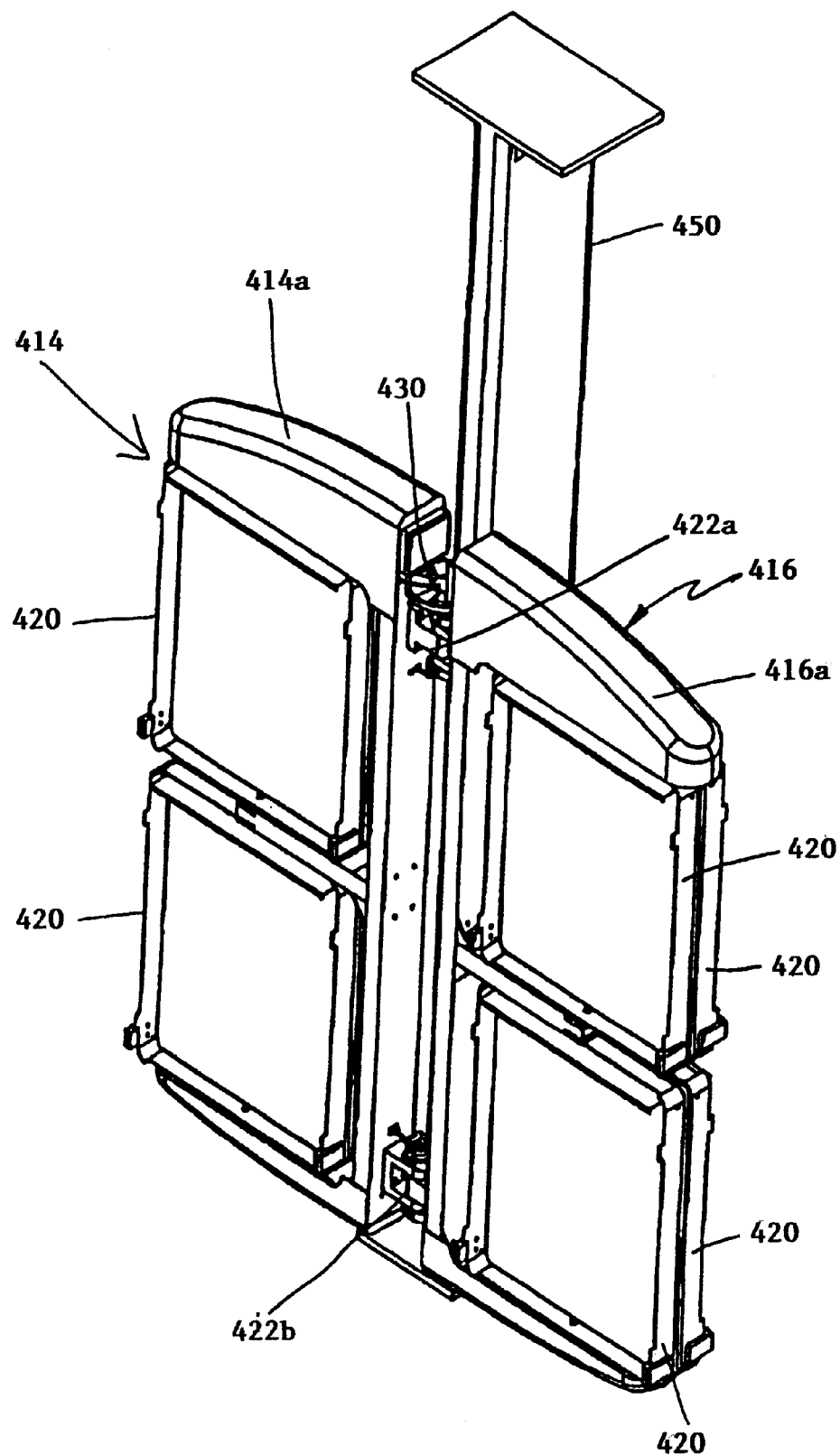
Figure 5C:
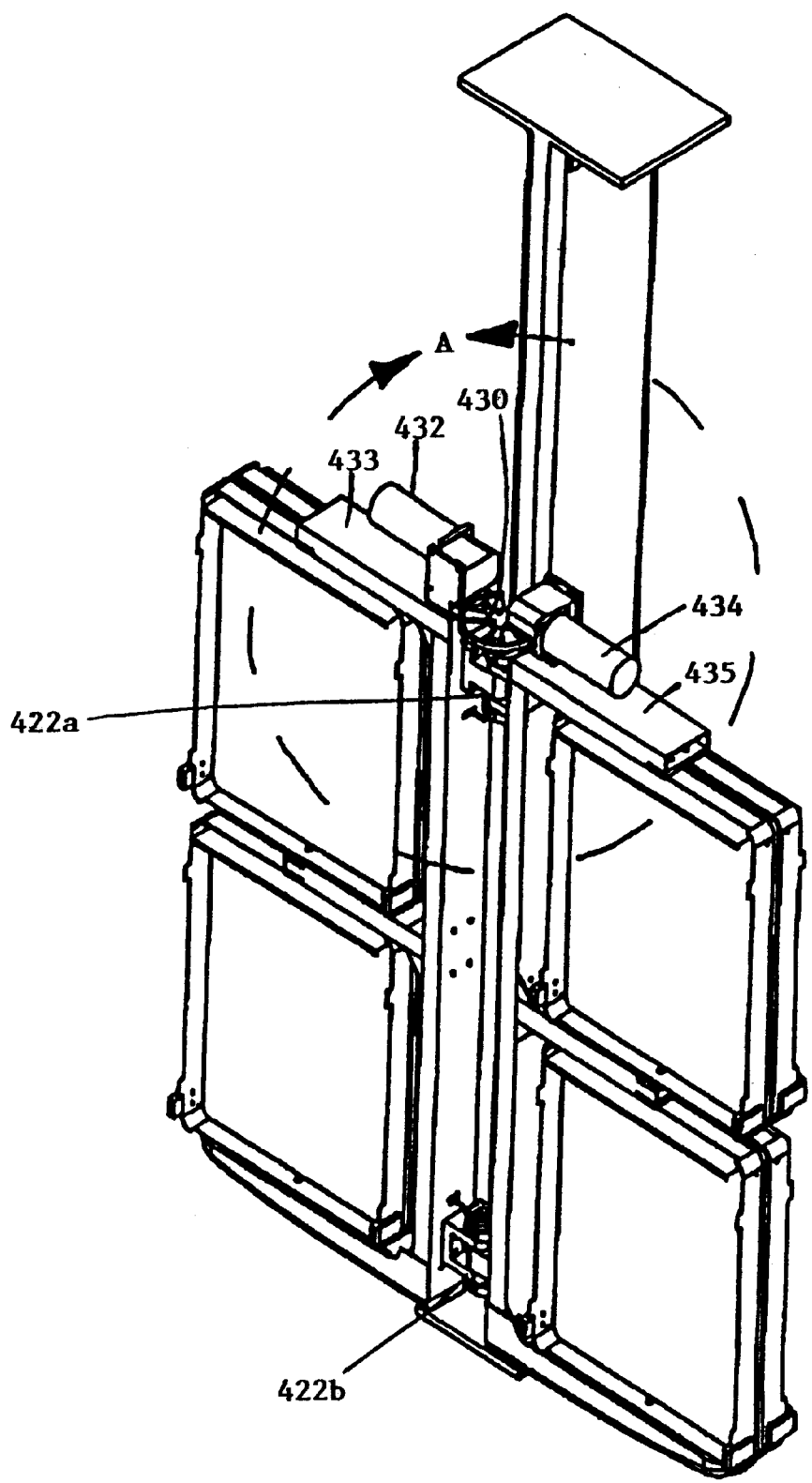
Figure 5D:
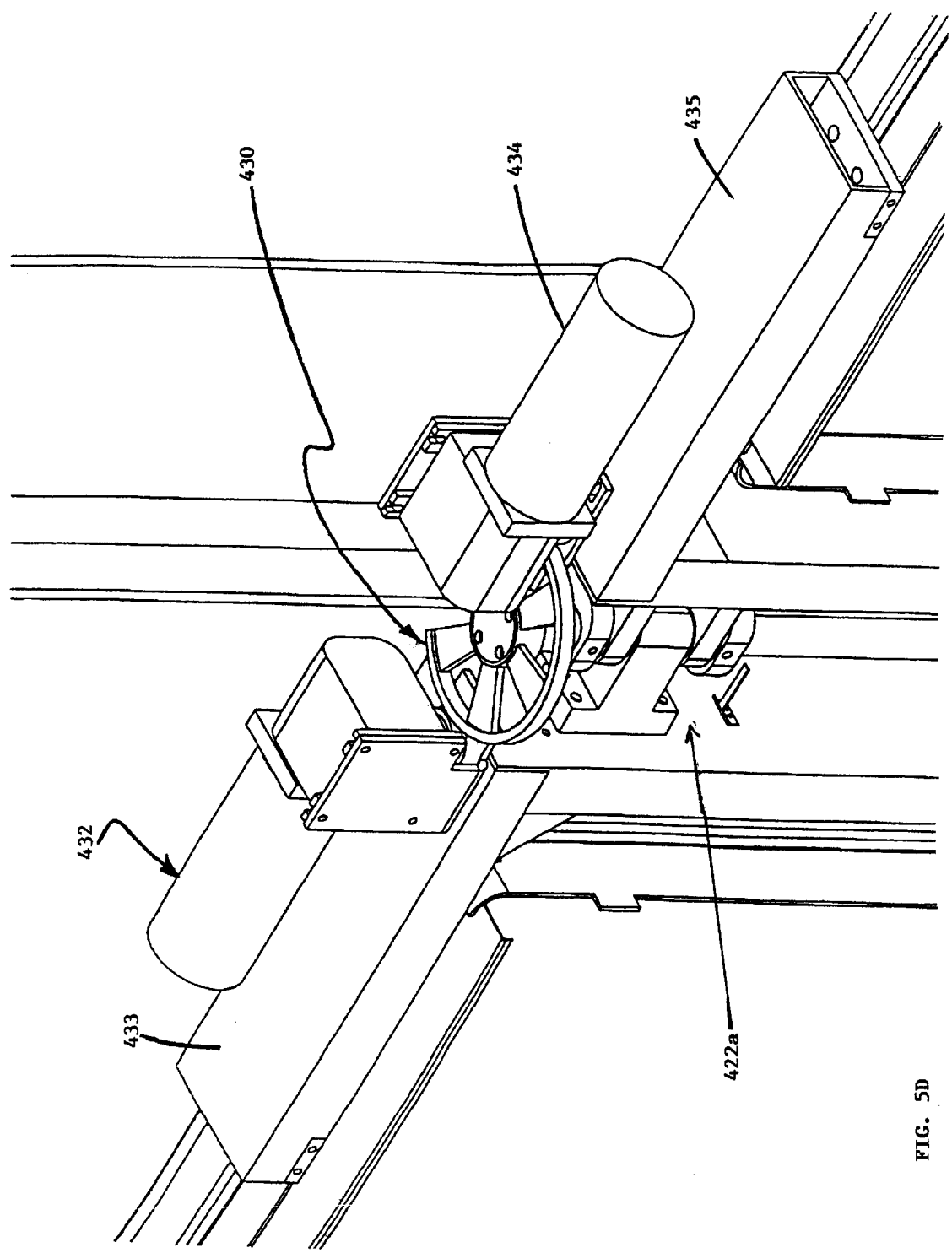
FIGS. 5D–5E show close-up views of the collimator exchanger shown in FIGS. 5A–5C.
Figure 5E:
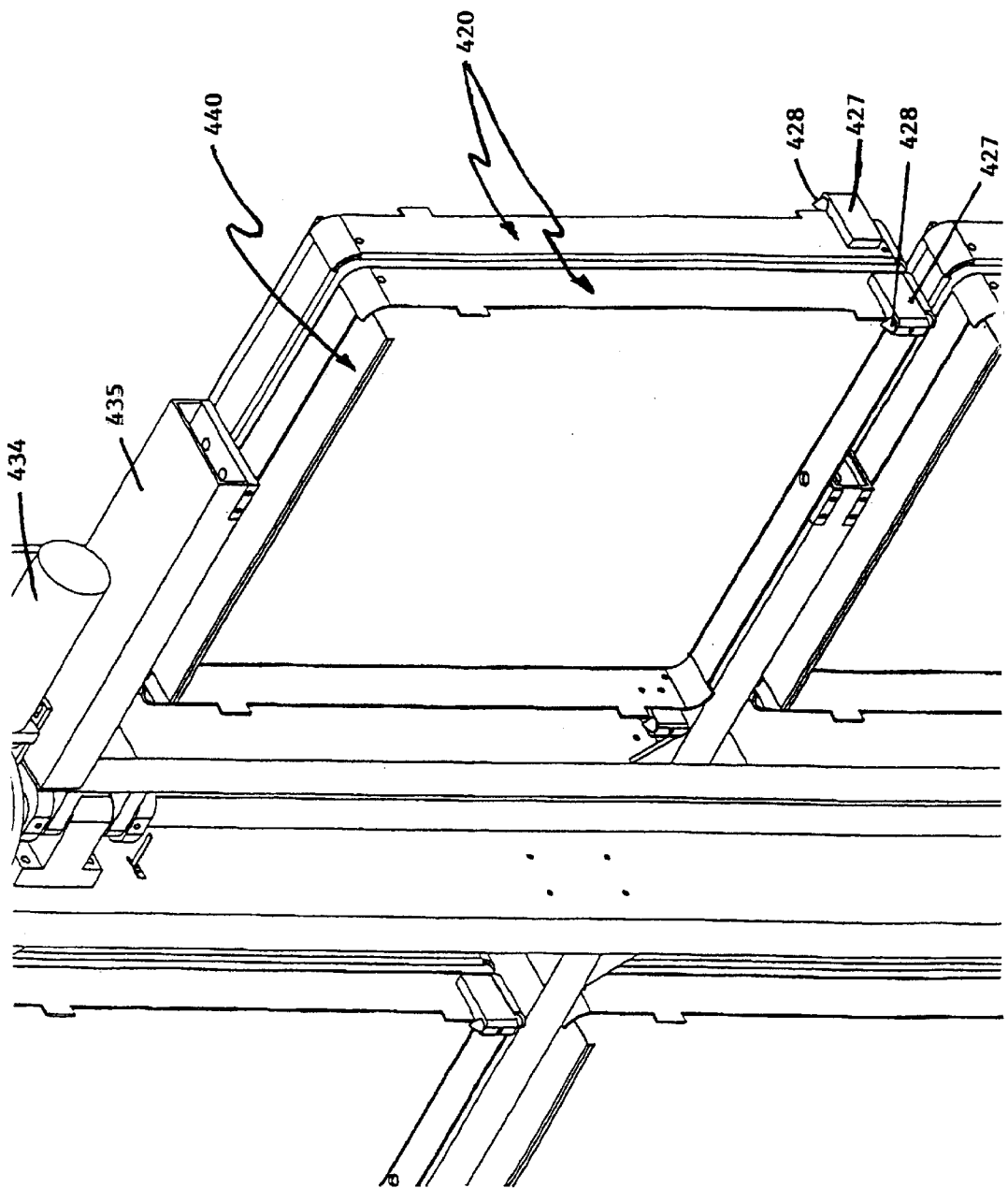

FIGS. 5A–5E show another embodiment of a collimator exchanger according to the present invention. Gates 414 and 416 are attached to support column 450 by hinge joints 422a and 422b. Both gates 414 and 416 are coupled to a fixed gear 430 attached to post 450. Gates 414 and 416 each have collimator trays 420 arranged back-to-back to allow two collimator exchanges to be performed concurrently. In FIG. 5A, gate 414 is shown in its home or closed position, and gate 416 is shown in its exchange or open position. In FIG. 5B, gates 414 and 416 are both shown in their home positions. When gates 414 and 416 are both in their home positions, the exchanger maintains a thin profile that reduces the area occupied by the exchanger. In FIG. 5C, gates 414 and 416 are shown without top covers 414a and 416a, respectively. Detail A is shown in FIG. 5D. Housed within top covers 414a and 416a are worm gear motors 432 and 434 attached to arms 433 and 435, respectively, of gates 414 and 416, respectively. Worm gear motors 432 and 434 are each coupled to fixed gear 430 to independently rotate their respective gates between their home and exchange positions. As shown in FIG. 5E, a latch 440 extends out from a top edge of each tray 420 to prevent a collimator from falling out of tray 420. Pins 428 on tabs 427 engage lower receiving holes in collimator tabs (see FIG. 4C, for example) to further secure a collimator in tray 420.

Figure 6:
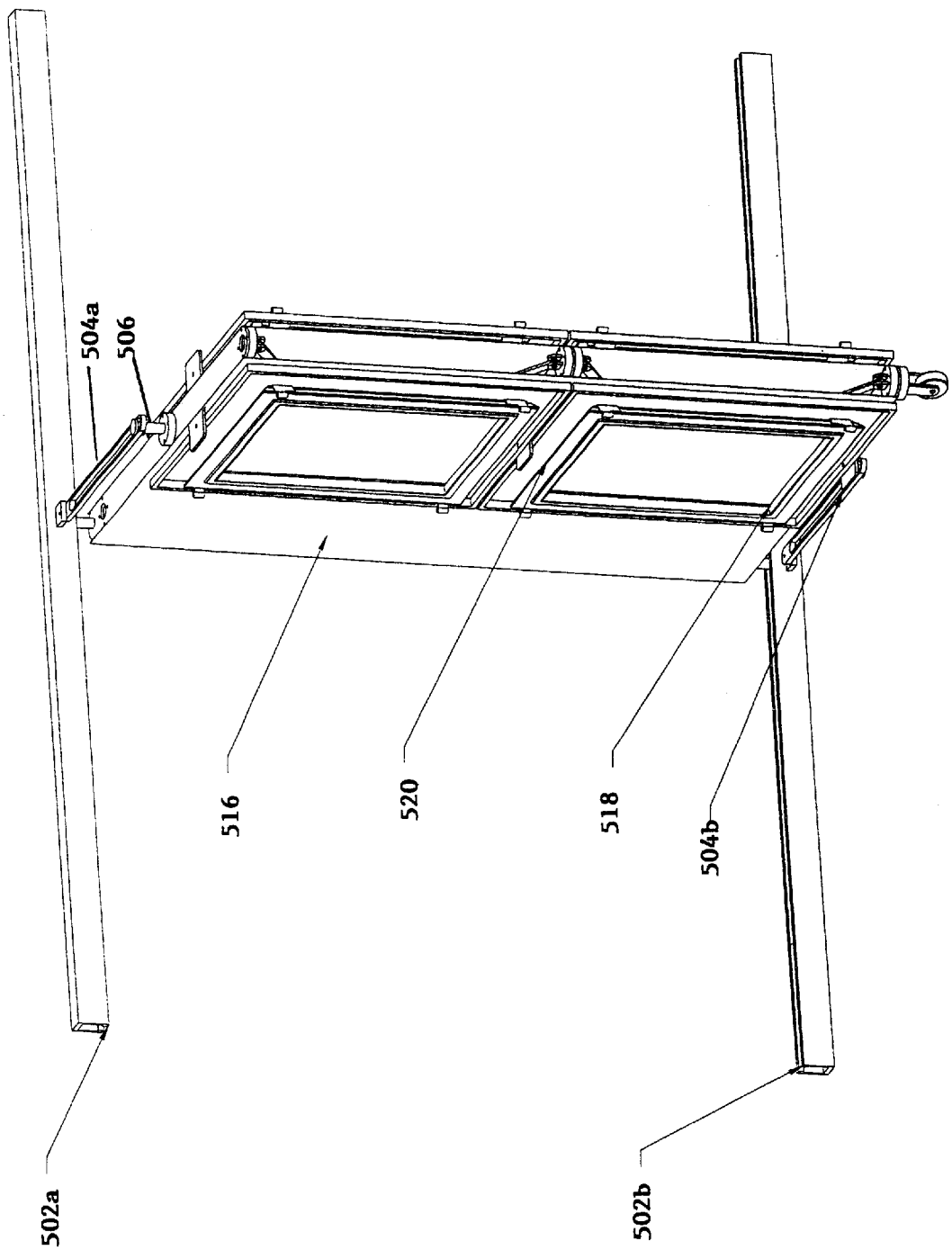
FIG. 6 shows yet another collimator exchanger in accordance with the teachings of the present invention.

FIG. 6 shows yet another embodiment of a collimator exchanger according to the present invention. A gate 516 is coupled to a top main track 502a and a bottom main track 502b to allow gate 516 to slide along tracks 502a and 502b. Collimator carriers 520 are coupled to gate 516 and house collimators 518, such as those used in conjunction with gamma ray detectors. Pins 506 extending from top and bottom edges of gate 516 engage guide tracks 504a and 504b which are hinged are one of their ends to tracks 502a and 502b, respectively, at fixed points. Guide tracks 504a and 504b help rotate gate 516 between its home position and its exchange position as shown in FIGS. 7A–7D.

FIG. 7A shows gate 516 slightly offset from its home position. Guide track 504a is substantially parallel to main track 502a when gate 516 is in its home position. FIGS. 7B and 7C show gate 516 sliding along main track 502a while also rotating in a direction opposite to the rotation of guide track 504a. Guide track 504a helps rotate gate 516 by guiding pin 506 as gate 516 is also sliding along main track 502a. In FIG. 7D, gate 516 is shown in its exchange position, in which gate 516 is substantially perpendicular to main track 502a.

In the previously described embodiments of the present invention, the gates have been described as rotating between their home and exchange positions. However, it is appreciated that the gates can be moved between their home and exchange positions with purely translational movement. For example, the gates could slide in and out of a slot in a wall adjacent to the gantry.

In the foregoing detailed description, the apparatus and method of the present invention have been described with reference to specific exemplary embodiments. For example, radiation detectors and collimators have been referenced in describing several of the embodiments of the present invention. However, it is appreciated that the present invention is not limited to the use of radiation detectors and collimators. In fact, it will be evident that various modifications and changes may be made without departing from the broader scope and spirit of the present invention. The present specification and figures are accordingly to be regarded as illustrative rather than restrictive.

What is claimed is:

1. A collimator exchange system comprising:
a first frame having a plurality of co-planar receptacles, a collimator mateable to at least one of said plurality of co-planar receptacles; and
a second frame having a first docking member, said first docking member positionable adjacent to said at least one of said plurality of co-planar receptacles such that said first docking member can contact said collimator to unmate said collimator from said at least one of said plurality of co-planar receptacles.

2. A system as in claim 1 wherein said first docking member comprises a protrusion and said collimator comprises an indentation, said protrusion mateable with said indentation to align said collimator with said first docking member when said collimator is unmated from said first receptacle.

3. A system as in claim 1 wherein said collimator is mated to said first docking member concurrently with said unmating of said collimator from said at least one of said plurality of co-planar receptacles.

4. A system as in claim 1 wherein said at least one of said plurality of co-planar receptacles and said first docking member are independently movable.

5. A system as in claim 1 wherein said at least one of said plurality of co-planar receptacles comprises a securing member to hold in place said collimator when said collimator is mated to said at least one of said plurality of co-planar receptacles.

6. A system as in claim 1 wherein said first frame comprises a positioning arm, said at least one of said plurality of co-planar receptacles coupled to said positioning arm.

7. A system as in claim 6 wherein said positioning arm is capable of rotational movement.

8. A system as in claim 1 wherein said second frame comprises a positioning arm, said first docking member coupled to said positioning arm.

9. A system as in claim 8 wherein said positioning arm is capable of translational movement.

10. A system as in claim 1 wherein said first docking member houses a radiation detector.

11. An apparatus for transferring collimators, said apparatus comprising:
a housing;
a first transfer member movably coupled to said housing;
a second transfer member movably coupled to said housing; and
a rotatable delivery arm having a first side and a second side, a first collimator of a first plurality of collimators being coupled in a co-planar arrangement to said first side, a second collimator of a second plurality of collimators being coupled in a co-planar arrangement to said second side.

12. An apparatus as in claim 11 wherein said delivery arm rotates from a first position to a second position when at least one of said first and second collimators is to be transferred, and wherein when said delivery arm is in said second position, one of said first and second transfer members is disposed adjacent to said at least one of said first and second collimators.

13. An apparatus as in claim 12 wherein if both of said first and second collimators are to be transferred, said first and second transfer members concurrently uncouple from said delivery arm said first and second collimators, respectively, while said delivery arm is in said second position.

14. An apparatus as in claim 13 wherein said delivery arm rotates from said second position to said first position when said first and second collimators have been uncoupled from said delivery arm.

15. An apparatus as in claim 12 wherein if only one of said first and second collimators is to be transferred, one of said first and second transfer members uncouples from said delivery arm said one of said first and second collimators while said delivery arm is in second position.

16. An apparatus as in claim 15 wherein said delivery arm rotates from said second position to said first position when said one of said first and second collimators has been uncoupled from said delivery arm.

17. An apparatus as in claim 11 wherein said first transfer member, said second transfer member, and said delivery arm are independently movable.

18. An apparatus as in claim 11 wherein said delivery arm is capable of translational and rotational movement.

19. A method for transferring collimators, said method comprising:
moving a gate containing a plurality of collimator carriers from a first position to a second position;
positioning a docking arm adjacent to a predetermined one of said plurality of collimator carriers;
unloading a collimator from said predetermined one of said plurality of collimator carriers to said docking arm; and
removing said gate from said second position to said first position.

20. A method as in claim 19 further comprising securing said collimator to said docking arm.

21. A method as in claim 20 further comprising repositioning said docking arm away from said predetermined one of said plurality of collimator carriers, said repositioning performed after said securing and before said removing.

22. A method as in claim 19 wherein said predetermined one of said plurality of collimator carriers moves through a rotational path.

23. A method for transferring collimators, said method comprising:
moving a collimator carrier from a first position to a second position;
positioning a docking arm adjacent to said collimator carrier;
unloading a collimator from said collimator carrier to said docking arm; and removing said collimator carrier from said second position to said first position; wherein said collimator carrier moves concurrently through a translational path and a rotational path.

24. An apparatus for exchanging a collimator in a nuclear medicine imaging system, said apparatus comprising:
delivery means for moving a plurality of collimator carriers from a first position to a second position, the plurality of collimator carriers being co-planar;
positioning means for moving a docking arm adjacent to a predetermined one of said collimator carriers; and
transferring means for unloading a collimator from said predetermined one of said collimator carriers to said docking arm.

25. An apparatus as in claim 24 further comprising securing means for securing said collimator to said docking arm.

26. An apparatus as in claim 24 further comprising actuating means for rotating said delivery means between said first position and said second position.

27. A collimator exchange system comprising:

a first frame having a plurality of co-planar receptacles, a collimator mateable to at least one of said plurality of co-planar receptacles;

a second frame having a first docking member, said first docking member positionable adjacent to said at least one of said plurality of co-planar receptacles such that said first docking member can contact said collimator to unmate said collimator from said at least one of said plurality of co-planar receptacles; and a plurality of sensors disposed within the receptacles and collimators.

28. The systems of claim 27, wherein the sensors comprise Hall effect sensors.

* * * * *